(12) United States Patent　　(10) Patent No.: US 9,090,937 B2
Marionnet et al.　　(45) Date of Patent: Jul. 28, 2015

(54) EPIDERMAL DIFFERENTIATION MICRORNA SIGNATURE AND USES THEREOF

(75) Inventors: Claire Marionnet, Ville D'Avray (FR); Francoise Bernerd, Nice (FR)

(73) Assignee: L'OREAL, Paris (FR)

( * ) Notice: Subject to any disclaimer, the term of this patent is extended or adjusted under 35 U.S.C. 154(b) by 75 days.

(21) Appl. No.: 13/392,768

(22) PCT Filed: Sep. 2, 2010

(86) PCT No.: PCT/EP2010/062891
§ 371 (c)(1),
(2), (4) Date: Mar. 1, 2012

(87) PCT Pub. No.: WO2011/026909
PCT Pub. Date: Mar. 10, 2011

(65) Prior Publication Data
US 2012/0259000 A1　　Oct. 11, 2012

Related U.S. Application Data

(60) Provisional application No. 61/239,154, filed on Sep. 2, 2009.

(30) Foreign Application Priority Data

Dec. 1, 2009　(FR) ..................................... 09 05789

(51) Int. Cl.
*C12Q 1/68*　　(2006.01)
*A61K 8/60*　　(2006.01)
*A61Q 19/00*　　(2006.01)
*A61Q 19/08*　　(2006.01)

(52) U.S. Cl.
CPC .............. *C12Q 1/6881* (2013.01); *A61K 8/606* (2013.01); *A61Q 19/00* (2013.01); *A61Q 19/007* (2013.01); *A61Q 19/08* (2013.01); *C12Q 1/6883* (2013.01); *C12Q 2600/158* (2013.01); *C12Q 2600/178* (2013.01)

(58) Field of Classification Search
USPC ............. 435/6.11, 91.1; 506/9, 16; 514/44 A; 536/23.1
See application file for complete search history.

(56) References Cited

U.S. PATENT DOCUMENTS

2009/0143326 A1　6/2009 Obad et al.
2009/0186348 A1　7/2009 Huibregtse et al.
2010/0202973 A1　8/2010 Pivarcsi et al.
2010/0216139 A1*　8/2010 Galas et al. ........................ 435/6
2010/0280099 A1　11/2010 Elmén
2010/0285073 A1　11/2010 Olson et al.
2010/0298410 A1　11/2010 Obad et al.

2012/0207744 A1*　8/2012 Mendlein et al. .......... 424/130.1
2012/0219632 A1*　8/2012 Lim .............................. 424/520
2013/0184175 A1*　7/2013 Beaudenon-Huibregtse et al. .................................. 506/9

FOREIGN PATENT DOCUMENTS

WO　WO 2008/142567 A2　11/2008
WO　WO 2009/018493 A1　2/2009
WO　WO 2009/036332 A1　3/2009
WO　WO 2009/043353 A2　4/2009
WO　WO 2009/148137 A1　12/2009
WO　WO 2010/018585 A2　2/2010

OTHER PUBLICATIONS

Yi et al., Nature Genetics, vol. 38, No. 3, pp. 356-362 (2006).*
Wenguang et al, J. Integrative Biology, vol. 11, No. 4, pp. 385-396 (2007).*
Aberdam et al., Trends in Biochem. Sci., vol. 33, No. 12, pp. 583-591 (2008).*
Preliminary French Search Report issued Jul. 22, 2010, in FR 0905789 with English translation of Category of Cited Documents.
International Search Report issued Feb. 24, 2011, in PCT/EP2010/062891 with English translation of category of cited documents.
Marilena V. Iorio, et al., "Micro RNA Signatures in Human Ovarian Cancer", Cancer Research, vol. 67, No. 18, XP-002593221, Sep. 15, 2007, pp. 8699-8707.
Tomohiro Itoh, et al., MicroRNA-141 and-200a Are Involved in Bone Morphogenetic Protein-2-induced Mouse Pre-osteoblast Differentiation by Targeting Distal-less Homeobox $5^{Sx}$, Journal of Biological Chemistry, vol. 284, No. 29, XP-002593222, Jul. 17, 2009, pp. 19272-19279.
Enikö Sonkoly, et al., "Protein Kinase C-Dependent Upregulation of miR-203 Induces the Differentiation of Human Keratinocytes", The Journal of Investigative Dermatology, vol. 130, No. 1, XP-002593223, Jan. 2010, pp. 124-134.
Am Lena, et al., "miR-203 represses 'stemness' by repressing ΔNp63", Cell Death and Differentiation, vol. 15, No. 7, XP-002593224, Jul. 2008, pp. 1187-1195.
Lin Shin-Lung, et al., "Chapter 4: Recent Application of Intronic MicroRNA Agents in Cosmetics", Current Perspectives in microRNAs (miRNA), XP-009136584, Jan. 1, 2008, pp. 51-72.

(Continued)

*Primary Examiner* — Jane Zara
(74) *Attorney, Agent, or Firm* — Oblon, McClelland, Maier & Neustadt, L.L.P.

(57) ABSTRACT

The present invention concerns a method for determining the state of epidermal differentiation of a human keratinocyte in a sample of human epithelium, comprising determining the level of expression of at least one miRNA selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425, hsa-miR-92b, hsa-let-7i, hsa-miR-22, hsa-miR-221, hsa-miR-222, hsa-miR-29a, hsa-miR-29b, hsa-miR-663, hsa-miR-30a and hsa-miR-30c within said keratinocyte and comparing the level of expression of the selected miRNA or miRNAs with the mean level of expression of the selected miRNA or miRNAs in non-differentiated keratinocytes, or in differentiated epidermal keratinocytes, preferably originating from the same strain or from the same population. The present invention also concerns various uses of the method for determining the state of epidermal differentiation as well as pharmaceutical or cosmetic compositions.

7 Claims, No Drawings

(56) References Cited

OTHER PUBLICATIONS

Daniel Aberdam, "miRNAs, 'stemness' and skin", Trends in Biochemical Sciences, vol. 33, No. 12, XP-025691283, Dec. 1, 2008, pp. 583-591.

Clive R. Harding, "The stratum corneum: structure and function in health and disease", Dermatologic Therapy, vol. 17 Suppl. 1, XP-002593225, 2004, pp. 6-15.

Joseph Mazar, et al., "Protein-coding and non-coding gene expression analysis in differentiating human keratinocytes using a three-dimensional epidermal equivalent", Molecular Genetics and Genomics, vol. 284, No. 1, XP-002593226, Jul. 2010, pp. 1-9.

David P. Bartel, et al., "MicroRNAs: Genomics, Biogenesis, Mechanism, and Function", Cell, vol. 116, Jan. 23, 2004, pp. 281-297.

Ines Alvarez-Garcia, et al., "MicroRNA functions in animal development and human disease", Development, vol. 132, (21), 2005, pp. 4653-4662.

Kathryn A. O'Donnell, et al., "c-Myc-regulated microRNAs modulate E2F1 expression", Nature, vol. 435/9, Jun. 2005, pp. 839-843.

Francesco Fazi, et al., "A Minicircuitry Comprised of MicroRNA-223 and Transcription Factors NFI-A and C/EBPα Regulates Human Granulopoiesis", Cell, 123, Dec. 2, 2005, pp. 819-831.

Rui Yi, et al., "Morphogenesis in skin is governed by discrete sets of differentially expressed microRNAs", Nature Genetics, vol. 38, No. 3, Mar. 2006, pp. 356-362.

Zhang Wenguang, et al., "A Subset of Skin-Expressed microRNAs with Possible Roles in Goat and Sheep Hair Growth Based on Expression Profiling of Mammalian microRNAs", OMICS A Journal of Integrative Biology, vol. 11, No. 4, 2007, pp. 385-396.

Rui Yi, et al., "A skin microRNA promotes differentiation by repressing 'stemness'", Nature, vol. 452/13 Mar. 2008, pp. 225-229.

Enikö Sonkoly, et al., "MicroRNAs: Novel Regulators Involved in the Pathogenesis of Psoriasis?", PlosONE, Jul. 2007, Issue 7, 2:e610, pp. 1-8.

Federica Felicetti, et al, "The Promyeloyitic Leukemia Zinc Finger-MicroRNA-221/-222 Pathway Controls Melanoma Progression through Multiple Oncogenic Mechanisms", Cancer Res. 68: (8), Apr. 15, 2008, pp. 2745-2754.

Akemi Ishida-Yamamoto, et al., "Inherited Disorders of epidermal keratinization", Journal of Dermatological Science, 18, 1998, pp. 139-154.

S. Hoffjan, et al., "On the role of the epidermal differentiation complex in ichthyosis vulgaris, atopic dermatitis and psoriasis", British Journal of Dermatology, 157, 2007, pp. 441-449.

Ruby Ghadially, et al., "The aged Epidermal Permeability Barrier Structural, Functional, and Lipid Biochemical Abnormalities in Humans and a Senescent Murine Model", The Journal of Clinical Investigation. Inc., vol. 95, May 1995, pp. 2281-2290.

Claire Marionnet, et al., "Modulation of Gene Expression Induced in Human Epidermis by Environmental Stress in Vivo", The Journal for Investigative Dermatology, 121, 2003. pp. 1447-1458.

Caifu Chen, et al., "Real-time quantification of microRNAs by stem-loop RT-PCR", Nucleic Acids Research, vol. 33, No. 20, e179, Nov. 27, 2005, pp. 1-9.

Vasily V. Vagin, et al., "A Distinct Small RNA Pathway Silences Selfish Genetic Elements in the Germline", Science, vol. 313, Jul. 21, 2006, pp. 320-324.

Shuji Takada, et al., "Mouse microRNA profiles determined with a new and sensitive cloning method", Nucleic Acids Research,vol. 34, No. 17, e115, Published online Sep. 14, 2006, pp. 1-8.

* cited by examiner

EPIDERMAL DIFFERENTIATION MICRORNA SIGNATURE AND USES THEREOF

This application is a National Stage of PCT/EP10/062891 filed Sep. 2, 2010 and claims the benefit of U.S. 61/239,154 filed Sep. 2, 2009 and FR 0905789 filed Dec. 1, 2009.

The present invention relates to the field of cosmetics and pertains to the skin. More generally, it relates to the context of characterizing the state of epidermal differentiation of the skin and the treatment of ailments, illnesses or pathologies linked to epidermal differentiation.

The epidermis is a multilayered epithelium which acts as a protective barrier against its environment and challenges against it. It is primarily composed of keratinocytes which proliferate in the deepest layer of the epidermis then start to differentiate, migrating from the depths to the surface of the epidermis. At the surface of the epidermis, the most differentiated keratinocytes, known as corneocytes, constitute the stratum corneum, which is highly protective. Thus, the epidermis is both the seat of cellular multiplication, which takes place inside the basal layer, and also the seat of cell differentiation, within the intermediate layer, which results in the formation of a well-differentiated protective structure, the stratum corneum. The complete cycle takes about 20 days. That programme corresponds to the expression of many specific genes which are successively activated then inhibited in a sequential, coordinated manner. That programme involves a large number of transcription factors, enzymes, lipids and structural proteins. Numerous growth factors, calcium, vitamin A and D3 derivatives are important regulators of keratinocyte proliferation and differentiation. Certain physiological or pathological states, and even certain challenges to the surface of the skin or through the blood circulation, lead to a deregulation of that process of epidermal differentiation which is temporally and spatially coordinated.

In skin pathologies associated with modifications to the epidermal differentiation programme, it has been observed many diseases, which may or may not be genetic [14-15], such as psoriasis, atopic dermatitis, acne, ichthyoses, Netherton syndrome, pityriasis rubra pilaris, keratosis pilaris, Darier's disease, palmoplantar keratoderma and porokeratoses.

Examples of more physiological circumstances associated with modifications to epidermal differentiation are: age, with anomalies in terminal differentiation and a reduction in the barrier function [17], scarring which is characterized by a phase for modification of epidermal homeostasis (hyperproliferation, migration, re-epithelialization and restoration of terminal differentiation), and age-related or winter-related xeroses (dry skin, with squamous accumulation processes) [18].

Examples of perturbations due to external factors causing disorders of the epidermal differentiation process that may be mentioned [19] are: exposure to solar UV radiation, to heat, to exfoliating agents, desquamating agents, delipidizing agents, or mechanical challenges.

In the case of slight disorders, emollients and keratolytics are recommended. Such treatments do not act on the proliferation/differentiation balance, but are intended to make the lesions tolerable for the patient and they usually only have a suspensive effect.

For more severe disorders, retinoic acid and its derivatives, vitamin D3, which may regulate the proliferation and differentiation of keratinocytes, have been used for a number of years. In some cases, methotrexate and cyclosporin are also recommended. All of such treatments have major side effects, which are very burdensome for the patients.

In order to characterize the state of epidermal differentiation of skin or of a cultivated epithelium of the "reconstructed skin" type and in order to be able to evaluate molecules which might modulate the epidermal differentiation process, the following technical tools are currently available:

morphological analysis and biochemical markers of the stages of epidermal differentiation (immunohistochemistry). This technique can only be used to analyze, either very generally (topographic histology), or marker by marker (immunohistochemistry), the known protein protagonists in differentiation. It cannot produce a signature of the state of the skin. It is unwieldy and necessitates having certain tools available such as antibodies which are specific for the markers under investigation, which is not always the case. Further, it is a technique which is not readily quantitative;

transcriptome analysis: this method is widely used to obtain molecular signatures of healthy or diseased tissue. This technique is based on an analysis of the expression of mRNA transcripts of a sample. It may be very general, using DNA chips which may contain up to 12000 genes. However, it suffers from some disadvantages, in particular requiring expensive equipment (like the Affymetrix™ system), but above all it generates a very large amount of data which is frequently difficult to handle and has to be processed by a high performance bioinformatics service;

proteome analysis: this provides a global picture of the general location of all of the proteins present in a tissue. It still uses a plurality two-dimensional electrophoresis gel techniques and thus is very unwieldy in execution. Furthermore, accurate identification of the proteins necessitates supplemental steps and very expensive equipment requiring particular skill and expertise to operate.

Thus, there is a need for a method which can easily and rapidly characterize the state of epidermal differentiation of skin or cultivated epithelium.

The present inventors have brought to light, completely unexpectedly, the existence of a microRNA signature of epidermal differentiation, which not only can be used to characterize the state of epidermal differentiation, but also can be used to envisage various treatments for ailments linked to deregulation of said state of differentiation.

MicroRNAs (miRNAs), which were discovered in 1993, are short endogenous RNAs which are involved in interference by RNA: they can target messenger RNA (mRNA) and generate their degradation or prevent their translation. Such microRNAs thus play very important regulation roles in the cell. Further, they constitute one of the most abundant classes of regulatory molecules. They are endogenous in origin, derived from pri-miRNA encoded by the genome. To date, approximately 700 human microRNAs have been identified. Their functions and targets have not all been elucidated or demonstrated.

They play a crucial role in the regulation of various cellular pathways and may be involved in human pathologies. MicroRNAs play a vital role in the regulation of development, differentiation, proliferation and apoptosis (for reviews, see [1] and [3]). As an example, in man, miR-17-5p and miR-20 are regulators for proliferation [4]; miR-223 is involved in granulopoiesis [5].

Deregulation of the expression of miRNAs may contribute to human pathologies. Certain miRNAs function as tumour suppressors; others function as oncogenes.

There are currently very few studies on miRNAs in skin, more particularly in human skin.

In animal skin, expressed miRNAs have been cloned, initially in the mouse. They play an important role in the morphogenesis of the epidermis and the coat [8]. More recently, miRNAs have been shown to be involved in coat growth in goats and sheep [10]. Very recently, in mouse skin, the miRNA miR203 has been identified as playing an important role in the induction of epidermal differentiation, by reducing the cell proliferation potential [11]. In man, the expression of miRNAs has been studied in normal skin and compared with that of skin with psoriasis and skin with eczema. The miRNA miR203 is highly expressed in the skin (compared with other organs) and only by keratinocytes. It has been identified as one of the miRNAs that is over-expressed in skin with psoriasis [12].

Finally, it has been shown that in man, certain miRNAs (miR-221 and miR-222) are involved in the control of melanoma progression [13].

Assuming that, for each miRNA, several tens of target genes exist, the present inventors propose:
  using miRNAs as markers for differentiation. Their much smaller number compared with messenger RNA means that miRNA profiles can be produced, for a location, or for a tissue, in a simpler, faster and cheaper manner than conventional general transcriptome methods;
  using the miRNA molecular signature of epidermal differentiation to identify modulators with a view to treatments of benign or more serious illnesses associated with disorders of epidermal differentiation. The term "modulators" means chemical entities or entities derived from natural extracts, complex formulations, siRNAs, miRNA inhibitors such as antagomirs, but also instrumental systems using light, mechanical effects on the skin, or injections;
  using miRNAs or modulators of said miRNAs with a view to cosmetic or therapeutic treatments in illnesses of epidermal differentiation or proliferation;
  using said miRNA signature to evaluate the efficacy of a cosmetic or therapeutic treatment for epidermal differentiation;
  using the miRNA molecular signature of epidermal differentiation to carry out a diagnostic on a normal or pathological epidermis.

To this end, the inventors propose using an assay of the expression of certain identified miRNAs.

Surprisingly, by systematic analysis of the expression of miRNAs in epidermal keratinocytes, the present inventors have shown that when the epidermal differentiation process is engaged and results in the formation of a stratum corneum, the human miRNAs miR-141, miR-148a, miR-182, miR-224, miR-26a, miR-26b, miR-361-5p, miR-425, miR-455-3p, miR-92b are over-expressed in the keratinocytes of the differentiated epidermis compared with proliferative non-differentiated keratinocytes not expressing the known epidermal differentiation markers and not forming corneocytes. These ten miRNAs thus represent a molecular signature of keratinocyte differentiation.

In contrast, in highly undifferentiated and proliferative keratinocytes, the human miRNAs let-7i, miR-22, miR-221, miR-222, miR-29a, miR-29b, miR-663, miR-30a, miR-30c are over-expressed in non-differentiated keratinocytes compared with the differentiated epidermis. These nine miRNAs represent, in contrast, a state of epidermal non-differentiation associated with intense proliferation.

Thus, the present invention concerns said miRNA signature of epidermal differentiation and various uses of said signature, in particular to evaluate or qualify a state of epidermal differentiation, as a novel diagnostic tool for a physiological or pathological differentiation disorder, as a target to correct a fault in epidermal differentiation or as a biomarker and screening tool to test epidermal differentiation modulating agents. The present invention also concerns the use of miRNAs of said signature, or modulators of said miRNAs, in therapeutic and cosmetic applications, especially in the form of compositions.

More particularly, in the context of the present invention, the terms below have the following meanings:

MicroRNA (or micro RNA or miRNA): microRNAs are single-stranded RNA approximately 20 to 25 nucleotides in length, more generally 21 to 24 nucleotides. miRNAs are repressors which act after transcription of a gene into mRNA: in fact, on pairing with messenger RNA, they guide their degradation or repress their translation into protein.

The production of miRNAs is under the tight control of a transcriptional and post-transcriptional regulation. The genes of miRNA are transcribed by RNA polymerase II into the form of long primary transcripts or precursors known as "pri-miRNA". The precursor miRNAs are cleaved enzymatically in the nucleus of the cell by a class 2 RNAase III (Drosha) to form "pre-miRNA"s. "Pre-miRNA" is a RNA with a length of approximately 70 nucleotides, folded into an imperfect stem-loop by base pairing between the first half and the second half of its sequence. The pre-miRNAs are then exported to the cytoplasm where they bind with another nuclease (Dicer) and the RISC complex (RNA-induced silencing complex) which contains the proteins TRBP (trans-activation-responsive RNA binding protein) and Ago2 (Argonaute 2). Upon binding, the protein Ago2 cleaves the 3' ends of the miRNA precursor, thereby generating the mature miRNA duplex. Only the specific strand of the target mRNA of the miRNA is retained (thermodynamic reaction) in the complex; the other strand is removed and degraded.

The target mRNA is then loaded into the RISC complex and degraded.

Although translational repression is the most observed silencing pathway observed in animal cells, recent studies show that miRNAs may also affect the quantity of target mRNA.

hsa-miRxx: this is the denomination for miRNAs identified in man (hsa meaning homo sapiens). The sequences for all of the known miRNAs are recorded in bases such as miRBase or microRNAdb, where they are identified by their unique accession number (xx). In the list below, the number hsa-miRxx is used to refer to the mature miRNA sequence.

In particular, the miRNAs below have the following sequences:

```
hsa-miR-141: mature miRNA:
                                           (SEQ ID N° 1)
UAACACUGUCUGGUAAAGAUGG hsa-miR-148a: mature miRNA:
                                           (SEQ ID N° 2)
UCAGUGCACUACAGAACUUUGU hsa-miR-182: mature miRNA:
                                           (SEQ ID N° 3)
UUUGGCAAUGGUAGAACUCACACU hsa-miR-224: mature miRNA:
                                           (SEQ ID N° 4)
CAAGUCACUAGUGGUUCCGUU
``` hsa-miR-26a (hsa-miR-26a-1 and hsa-miR-26a-2):
mature miRNA:

UUCAAGUAAUCCAGGAUAGGCU (SEQ ID N° 5)

hsa-miR-26b: mature miRNA:

UUCAAGUAAUUCAGGAUAGGU (SEQ ID N° 6)

hsa-miR-361-5p: mature miRNA:

UUAUCAGAAUCUCCAGGGGUAC (SEQ ID N° 7)

hsa-miR-425: mature miRNA:

AAUGACACGAUCACUCCCGUUGA (SEQ ID N° 8)

hsa-miR-455-3p: mature miRNA:

GCAGUCCAUGGGCAUAUACAC (SEQ ID N° 9)

hsa-miR-92b: mature miRNA:

UAUUGCACUCGUCCCGGCCUCC (SEQ ID N° 10)

hsa-let-7i: mature miRNA:

UGAGGUAGUAGUUUGUGCUGUU (SEQ ID N° 11)

hsa-miR-22: mature miRNA:

AAGCUGCCAGUUGAAGAACUGU (SEQ ID N° 12)

hsa-miR-221: mature miRNA:

AGCUACAUUGUCUGCUGGGUUUC (SEQ ID N° 13)

hsa-miR-222: mature miRNA:

AGCUACAUCUGGCUACUGGGU (SEQ ID N° 14)

hsa-miR-29a: mature miRNA:

UAGCACCAUCUGAAAUCGGUUA (SEQ ID N° 15)

hsa-miR-29b: mature miRNA:

UAGCACCAUUUGAAAUCAGUGUU (SEQ ID N° 16)

hsa-miR-663: mature miRNA:

AGGCGGGGCGCCGCGGGACCGC (SEQ ID N° 17)

hsa-miR-30a: mature miRNA:

UGUAAACAUCCUCGACUGGAAG (SEQ ID N° 18)

hsa-miR-30c: mature miRNA:

UGUAAACAUCCUACACUCUCAGC. (SEQ ID N° 19)

The prefix "hsa" has occasionally been omitted in the context of the present description. However, it designates the same 19 miRNAs described above.

Epidermal differentiation (keratinization or cornification): a phenomenon within the epidermis providing for continuous renewal of human skin. Epidermal differentiation covers all molecular, biochemical and morphological phenomena which provide for the transformation of the stem cell of the epidermis into an anucleated corneal cell or corneocyte, passing through the various stages of epidermal differentiation.

Said terminal differentiation allows for the constitution of specialized structures such as the stratum corneum providing the organism with an effective barrier against the environment. During epidermal differentiation, the keratinocytes of the deepest layer of the epidermis divide to give rise to two identical daughter cells, one of which remains in place while the second migrates towards the upper layer, the differentiation layer, while undergoing morphological and biochemical modifications.

Non-differentiated keratinocytes (or undifferentiated keratinocytes), or basal keratinocytes (or of the basal layer): keratinocytes expressing the keratins K5 and K14, and having a mitotic activity.

Differentiated keratinocytes: keratinocytes no longer having mitotic activity and having commenced terminal differentiation, in particular by induction of the keratins K1 and K10.

Antagomir: this is a novel class of chemically synthesized oligonucleotides. They are used to silence the action of endogenous miRNAs. An antagomir is a short synthetic RNA molecule which is completely complementary to a target miRNA with one or more base modifications to inhibit cleavage by Ago2 (other modifications are also frequently introduced in addition so that the antagomir is more resistant to degradation).

Antagomirs are frequently used to constitutively inhibit the activity of specific miRNAs. Many antagomirs have been published. All miRNAs are capable of being specifically inhibited by an antagomir.

The only information that is required is the sequence of the target miRNA in order to produce an antagomir which is capable of inhibiting the activity of said target miRNA.

Examples of other miRNA inhibitors are miRCURY LNA™ microRNA Knockdown Probes (Exiqon) or miScript miRNA inhibitors from Qiagen.

The present invention concerns a miRNA signature of epidermal differentiation, and thus a signature which is representative of the balance between proliferation and differentiation.

In a first aspect, the present invention more specifically concerns a method for determining the state of epidermal differentiation of a human keratinocyte in a sample of human epithelium. Such a method preferably comprises a step for determining the level of expression of at least one miRNA within said keratinocyte.

In accordance with the invention, the miRNA is selected from the following miRNAs identified by the inventors, namely from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425, hsa-miR-92b, hsa-let-7i, hsa-miR-22, hsa-miR-221, hsa-miR-222, hsa-miR-29a, hsa-miR-29b, hsa-miR-663, hsa-miR-30a and hsa-miR-30c. These 19 miRNAs are termed the microRNAs or miRNAs of the invention.

The level of expression of the selected miRNA is compared with the mean level of expression of said miRNA in non-differentiated keratinocytes, preferably non-differentiated keratinocytes under culture, or in differentiated epidermal keratinocytes.

There are many methods for detection and quantification of the miRNAs and they are familiar to the skilled person. Example 3 details the most widely used techniques.

Preferably, the method comprises determining the level of at least two distinct miRNAs selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425, hsa-miR-92b, hsa-let-7i, hsa-miR-22, hsa-miR-221, hsa-miR-222, hsa-miR-29a, hsa-miR-29b, hsa-miR-663, hsa-miR-30a and hsa-miR-30c, and comparing these two levels with the corresponding mean levels of the two selected miRNAs in non-differentiated keratinocytes, in particular in non-differentiated keratinocytes under culture, or in differentiated epidermal keratinocytes.

Alternatively, the method may comprise determining the level of expression of several miRNAs from among the 19 miRNAs of the invention, for example at least 3 or 5, or even 8, 10, 15, or even determining the level of expression of the 19 miRNAs of the invention and comparing the levels so determined with the mean degrees of expression of the corresponding miRNAs in non-differentiated keratinocytes, for example under culture, or in differentiated keratinocytes.

The term "mean level of expression of a miRNA in non-differentiated keratinocytes, especially non-differentiated keratinocytes under culture, or in differentiated epidermal keratinocytes" means the level of expression generally observed in this type of cell, preferably corresponding to the mean level of expression determined in at least 5 different keratinocytes, representative of the population of non-differentiated keratinocytes under culture, or representative of the population of differentiated epidermal keratinocytes. Preferably, it is the mean of at least 10 measurements, or even 20 or 100 different measurements.

Preferably, the non-differentiated keratinocytes under culture or differentiated epidermal keratinocytes in question are keratinocytes deriving from the same strain or the same population as the keratinocyte under study.

In the context of carrying out the method as mentioned above, the keratinocyte under study is considered to be differentiated or undergoing differentiation if the level of expression of at least one of the miRNAs selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b is statistically greater than the mean level of expression of said miRNA in non-differentiated keratinocytes, for example non-differentiated keratinocytes under culture.

The term "statistically greater" means that the difference observed is significant from a statistical point, in particular that it is greater than the standard deviation. A value is said to be statistically greater than another if the difference between the two values is greater than the uncertainty existing on the measurements.

Preferably, the upper level is at least 20% greater than the mean level, preferably greater by at least 50%. In accordance with particularly preferred embodiments, the level of expression of the selected miRNA or miRNAs is at least equal to one and a half times the mean level for said miRNA or miRNAs, preferably two or more times the mean level for the selected miRNA or miRNAs.

Preferably, the level of expression of at least one of the miRNAs selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b is statistically greater than all of the degrees of expression of said miRNA in all of the non-differentiated keratinocytes under culture which have been used to produce the mean level of expression of said miRNA.

In accordance with a preferred embodiment of the method of the invention, the mean level of at least two miRNAs selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b is greater than the mean level of expression of said miRNAs in non-differentiated keratinocytes. Preferably, this is the case for at least 3, or even 5 or 8, or even all of the miRNAs from the list consisting of hsa-miR-141, hsa-miR-148a, hsa-miR-182, hsa-miR-224, hsa-miR-26a, hsa-miR-26b, hsa-miR-361-5p, hsa-miR-425, hsa-miR-455-3p and hsa-miR-92b.

Alternatively, it could also be concluded that the keratinocyte being studied is differentiated or undergoing differentiation if the level of expression of at least one of the miRNAs selected from hsa-let-7i, hsa-miR-22, hsa-miR-221, hsa-miR-222, hsa-miR-29a, hsa-miR-29b, hsa-miR-663, hsa-miR-30a and hsa-miR-30c is substantially identical to the level of expression of said miRNA in differentiated epidermal keratinocytes. Preferably, this is the case for at least 2, or even 3, 5, 8 or all of the miRNAs selected from hsa-let-7i, hsa-miR-22, hsa-miR-221, hsa-miR-222, hsa-miR-29a, hsa-miR-29b, hsa-miR-663, hsa-miR-30a and hsa-miR-30c.

The term "substantially identical level" means that the difference in level observed is statistically insignificant, for example it is less than the uncertainty on the measurement of the level of expression of said miRNA.

In contrast, in the context of carrying out the method of the invention, it is considered that the keratinocyte being studied is a keratinocyte in a non-differentiated or slightly differentiated state if the level of expression of at least one of the miRNAs selected from hsa-let-7i, hsa-miR-22, hsa-miR-221, hsa-miR-222, hsa-miR-29a, hsa-miR-29b, hsa-miR-663, hsa-miR-30a and hsa-miR-30c is statistically greater than the mean level of expression of said miRNA in differentiated epidermal keratinocytes.

In a preferred embodiment, the mean level of at least two miRNAs selected from hsa-let-7i, hsa-miR-22, hsa-miR-221, hsa-miR-222, hsa-miR-29a, hsa-miR-29b, hsa-miR-663, hsa-miR-30a and hsa-miR-30c is greater than the mean level of expression of said miRNAs in differentiated epidermal keratinocytes. Preferably, this is the case for at least 3, or even 5 or 8, or even all of the miRNAs from the list consisting of hsa-let-7i, hsa-miR-22, hsa-miR-221, hsa-miR-222, hsa-miR-29a, hsa-miR-29b, hsa-miR-663, hsa-miR-30a and hsa-miR-30c. Alternatively, it could also be concluded that the keratinocyte being studied is in a non-differentiated state, also termed undifferentiated, or in a slightly differentiated state, if the level of expression of at least one of the miRNAs selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b is substantially identical to the level of expression of said miRNA in non-differentiated epidermal keratinocytes. Preferably, this is the case for at least 2, or even 3, 5, 8 or all of the miRNAs selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b.

The present invention also concerns a method for evaluating the differential in epidermal differentiation existing in a sample of human epithelium. Using said method, it is possible to characterize the state of differentiation of said sample, and thus, for example, to determine whether it is in a normal differentiation state for a healthy human epithelium or is characteristic of a pathology.

In accordance with this method of the invention, it is possible to determine the differential in epidermal differentiation existing between two layers of keratinocytes of said epithelium, i.e. the difference existing between these two layers in terms of epidermal differentiation, and hence to define whether a layer is in a more differentiated state than another layer of said epithelium, or the reverse in a more proliferative state.

The method of the invention for evaluating the differential in epidermal differentiation comprises a step for comparing, between two layers of keratinocytes in said epithelium, the level of expression of at least one miRNA selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425, hsa-miR-92b, hsa-let-7i, hsa-miR-22, hsa-miR-221, hsa-miR-222, hsa-miR-29a, hsa-miR-29b, hsa-miR-663, hsa-miR-30a and hsa-miR-30c.

In fact, as detailed above, the inventors have brought to light major differences in the level of expression existing in these 19 miRNAs, termed the miRNAs of the invention, within highly differentiated keratinocytes, and within non-differentiated keratinocytes. Studying the differences in the level of expression of these miRNAs thus means that the existence of a difference between the level of epidermal differentiation of a layer compared with another layer of keratinocytes of the epithelium being studied can be concluded.

Although it is possible to establish a difference in the level of expression of several miRNAs between the two layers, the differential in epidermal differentiation is brought to light as soon as there exists a significantly different level of expression in one layer compared with the other, for at least one of the miRNAs of the invention.

In accordance with this method, the differential in epidermal differentiation between the two layers is characterized in particular by greater expression of at least one of the miRNAs selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b in one layer compared with another. The difference in expression of said selected miRNA must be of an order of magnitude such that this difference is significant from a statistical viewpoint. Preferably, the difference in level of expression of the selected miRNA is by a factor of 1.3 or more, preferably 1.5 or more, or even by a factor of 2 or more.

In a preferred embodiment of the invention, the differential in epidermal differentiation between the two layers of the epithelium is characterized by greater expression of at least two different miRNAs selected from the list constituted by hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b in one layer compared with another, preferably at least 3, or even at least 5, or 8, or even greater expression of the ten miRNAs from this list. The difference in the level of expression of the miRNAs in one layer compared with another is not necessarily by an identical factor for all of the miRNAs from the list.

In accordance with this method, the differential in epidermal differentiation between the two layers may also be characterized by greater expression of at least one miRNA selected from hsa-let-7i, hsa-miR-22, hsa-miR-221, hsa-miR-222, hsa-miR-29a, hsa-miR-29b, hsa-miR-663, hsa-miR-30a and hsa-miR-30c in one layer compared with another. Once again, the difference in level of expression which is referred to means a difference which is significant from a statistical viewpoint.

Preferably, the difference in level of expression of the selected miRNA is by a factor of 1.3 or more, preferably 1.5 or more, or even by a factor of 2 or more.

In a preferred embodiment of the invention, the differential in epidermal differentiation between the two layers of the epithelium is characterized by greater expression of at least two different miRNAs selected from the list constituted by hsa-let-7i, hsa-miR-22, hsa-miR-221, hsa-miR-222, hsa-miR-29a, hsa-miR-29b, hsa-miR-663, hsa-miR-30a and hsa-miR-30c in one layer compared with another, preferably by at least 3, or even at least 5, or 8, or even the expression of the nine miRNAs from this list. The difference in the level of expression of the miRNAs in one layer compared with another is not necessarily by an identical factor for all of the miRNAs from the list.

In the context of the present invention, the sample of epithelium, of skin or epidermis in question may be from different sources; it may be from an epithelium under culture, for example a reconstituted epithelium of the "reconstructed skin" type or from a sample obtained from an individual, for example from a biopsy. Said sample may thus originate from human skin.

The comparison of the level of expression of at least one of the miRNAs of the invention may be carried out between any two layers of the epithelium sample being studied. If it is a sample of human skin, the comparison is preferably carried out between two opposed layers of keratinocytes, for example between the keratinocytes of the basal layer and those of the stratum corneum of the epithelium. It should be noted in this regard that recent studies indicate that corneocytes produce or contain miRNAs.

The comparison of the level of expression may also be carried out between two layers of the sample that are in fairly close proximity, for example in order to highlight the various stages of differentiation.

The present invention also concerns various applications of the characterization methods described above, and thus various uses of the miRNA signature highlighted by the inventors, in particular as a diagnostic tool of physiological or pathological differentiation disorders, as a target to correct a defect in epidermal differentiation or as a biomarker and screening tool to test epidermal differentiation modulator agents.

In a second aspect, the invention thus concerns a method for determining the efficacy of a treatment carried out on an epithelium. Such a method comprises comparing, before and after treatment, the miRNA signature of epidermal differentiation of the epithelium. Thus, the method comprises comparing the level of expression of at least one miRNA selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425, hsa-miR-92b, hsa-let-7i, hsa-miR-22, hsa-miR-221, hsa-miR-222, hsa-miR-29a, hsa-miR-29b, hsa-miR-663, hsa-miR-30a and hsa-miR-30c within keratinocytes of said epithelium, before and after treatment.

The inventors have in fact discovered a variation in the level of expression of these 19 miRNAs during the epidermal differentiation process occurring in the epidermis. The modification of the level of expression of at least one of said miRNAs is thus representative of a modification of the state of differentiation in response to the test treatment. Once again, a modification to the level of expression means a modification which is significant from a statistical viewpoint, and thus of a sufficient and reproducible intensity, observable on a substantial number of representative keratinocytes of the epithelium being studied. Alternatively, the method for determining the efficacy of a treatment applied to an epithelium in the context of the present invention may also comprise comparing, before and after the test treatment, the differential in epidermal differentiation of that epithelium. In accordance with this variation of the method, therefore, before treatment, the differential in epidermal differentiation existing between two layers of the epithelium is determined and the result obtained is compared with the differential in epidermal differentiation existing between these same two layers after treatment. Thus, a determination is made as to whether this test treatment has or has not modified the existing differential between two layers, for example by reducing the difference in the state of differentiation between the two layers, i.e. by reducing the differences in the degrees of expression of the miRNAs of the invention between the two layers, or by increasing the differential in epidermal differentiation.

The treatment tested by this method may consist of any treatment. Preferably, it concerns the topical application of a molecule, by application or by injection, preferably sub-cutaneously. The applied molecule may be a simple chemical entity or a combination or association of different entities, it may concern active principles, natural molecules, proteins, RNA, DNA, essential oil, a chemical entity from natural extracts, a complex formulation, a DNA molecule, a miRNA, a siRNA, a miRNA inhibitor, in particular an antagomir, etc.

Particular molecules which are particularly preferred in the context of the test treatment of the invention are RNAs, in particular miRNAs, or molecules modifying the expression of natural miRNAs, such as miRNA inhibitors, in particular antagomirs.

It may also concern the application of electromagnetic radiation, irrespective of the wavelength, for example visible, UV, IR or X rays. The treatment of the present invention also encompasses the application of various mechanical effects.

The method of the invention is considered to be effective if it causes a modification in the level of expression of at least one of the miRNAs of the invention in the epithelium being studied. Preferably, said treatment is considered to be effective if it causes a modification in the level of expression of at least two or even at least five of said miRNAs in the epithelium. Said treatment may cause a modification in the level of expression of at least 10, 15 or even the 19 miRNAs of the invention. The modifications caused in the level of expression of the miRNAs of the invention are not necessarily of identical amplitude for all of the miRNAs.

Preferably, in the context of the present invention, a test treatment will be considered to be effective if it causes a modification in the level of expression of at least one miRNA selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b concomitantly with a modification in the level of expression in the reverse direction to the above of at least one miRNA selected from hsa-let-7i, hsa-miR-22, hsa-miR-221, hsa-miR-222, hsa-miR-29a, hsa-miR-29b, hsa-miR-663, hsa-miR-30a and hsa-miR-30c. Thus, an effective treatment in the context of the invention will, for example, cause an increase in the level of expression of at least one miRNA selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b, and also simultaneously, a reduction in the level of expression of at least one miRNA selected from hsa-let-7i, hsa-miR-22, hsa-miR-221, hsa-miR-222, hsa-miR-29a, hsa-miR-29b, hsa-miR-663, hsa-miR-30a and hsa-miR-30c.

It is also possible, using the methods for determining the efficacy of the treatment of the present application, to quantify the beneficial action of an agent, in particular a cosmetic product, for example a cosmetic composition, as regards its action on the state of epidermal differentiation of the skin. The in vitro determination methods described above may in fact be used in a test protocol to determine the products that might be able to be qualified as an agent having an effect on the state of proliferation or differentiation of the keratinocytes of the skin. Further, using this test, it is possible to promote the product to consumers, by bringing to the fore the results obtained with that product using the determination methods described in the present invention. The evaluation of the effect on the state of epidermal differentiation will be based on a study of the expression of the miRNAs of the invention. Thus, the present invention also provides a method that can be used to recommend a product by indicating its effect in a test protocol constituted by a determination method as described above. Thus, the invention also pertains to a method for promoting a cosmetic product, consisting of determining an efficacy, action or property of said product demonstrated by at least one test carried out as described above.

Such a product could be promoted using any channel of communication. It may in particular be carried out by the sales assistant, directly at the point of sale, or by radio and television, in particular in the context of advertisements. It could also be made via the printed press or using any other document, in particular for publicity purposes (prospectuses). It could also be promoted via the interne, or via any other suitable computer network. It could also be made directly on the product, in particular on its packaging or any other explanatory notice which may be associated with it.

In a third aspect, the present invention also concerns various methods for screening molecules for their action on the epidermal differentiation process.

In particular, the invention concerns a method for screening modulators of the epidermal differentiation process in an epithelium, comprising evaluating the state of epidermal differentiation of keratinocytes in said epidermal, before and after application of the modulator to be screened.

Such screening processes may be carried out in vivo, or ex vivo, or in vitro, for example on epitheliums under culture or samples of epithelium.

The evaluation of the state of epidermal differentiation of keratinocytes in said epithelium is carried out using one of the methods according to the first aspect of the invention.

As described above, the epithelium referred to here may be an epithelium under culture, for example a reconstituted epithelium, of the "reconstructed skin" type, or a sample obtained from a human being, for example during a biopsy.

Alternatively, the invention also concerns a method for screening modulators of the epidermal differentiation process in an epithelium, comprising evaluating the differential in epidermal differentiation of said epithelium, before and after application of the modulator to be screened. The evaluation of the differential in epidermal differentiation of keratinocytes in said epithelium is carried out using one of the methods in accordance with the first aspect of the invention.

The modulator in question may be any chemical entity, for example derived from natural extracts or synthesized, it may be a complex formulation, a molecule of DNA, a miRNA, a siRNA or a miRNA inhibitor such as antagomir, for example. Clearly, this list is not exhaustive. Alternatively, the modulator may be an instrumental system using electromagnetic radiation, preferably visible, UV, IR or X radiation, or a system using mechanical effects.

In a fourth aspect, the present invention also concerns a method for diagnosing the state of an epidermis, by using the miRNA signature discovered by the inventors. Such a diagnostic method comprises determining the differential in epidermal differentiation existing in said epidermis between the basal layer and the stratum corneum, and comparing the mean differential in epidermal differentiation existing in a normal epidermis of the same type between the basal layer and the stratum corneum.

The determination of the differential in epidermal differentiation is preferably carried out using the various methods in accordance with the first aspect of the invention. It is preferably carried out on a sample of the epidermis of the skin to be diagnosed.

The mean differential in epidermal differentiation between the basal layer and the stratum corneum existing in a normal epidermis of the same type corresponds to a mean value of several measurements carried out on several epidermis samples from subjects with the same type of skin, which is healthy, as that of the epidermis to be diagnosed. The term "same type" means comparable age, ethnicity and identical colours. It is a mean value which corresponds to a "normal" or "healthy" state free of any pathology or lesion of the epidermis.

Using this diagnostic method establishes the miRNA profile of the skin to be diagnosed and by comparison, it may be diagnosed as suffering from premature ageing, photo-ageing or damage caused by solar radiation, ageing or damage caused by stress, acne or any other physiological or pathological ailment.

In accordance with another aspect, the present application also pertains to the use of an assay of the expression of at least one miRNA selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425, hsa-miR-92b, hsa-let-7i, hsa-miR-22, hsa-miR-221, hsa-miR-222, hsa-miR-29a, hsa-miR-29b, hsa-miR-663, hsa-miR-30a and hsa-miR-30c, in keratinocytes in a sample of the human epithelium to determine the state of epidermal differentiation of said keratinocytes.

The present inventors have in fact shown that this assay provides access to the miRNA signature of epidermal differentiation.

In a particularly preferred use, at least 2 distinct miRNAs out of the 19 miRNAs of the invention are assayed, preferably at least 5, 8, 10, 12 or 15. As an example, an assay of the 19 miRNAs of the invention may be used to determine the state of epidermal differentiation of the keratinocytes being studied.

In a yet another aspect, the application pertains to various uses, cosmetic and therapeutic, of at least one miRNA selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425, hsa-miR-92b, hsa-let-7i, hsa-miR-22, hsa-miR-221, hsa-miR-222, hsa-miR-29a, hsa-miR-29b, hsa-miR-663, hsa-miR-30a and hsa-miR-30c, and/or of at least one modulator of the expression of said miRNAs, and more particularly of an inhibitor of miRNA such as an antagomir.

In fact, because of the importance of said miRNAs in the epidermal differentiation process in skin, modulation of their level in the keratinocytes might influence epidermal differentiation, for example by slowing it down or, in contrast, speeding it up in order to slow down or speed up the stratum corneum renewal process. The modulation of the level of miRNAs of the invention within keratinocytes is more preferably carried out by introducing one or another of the miRNAs of the invention, in order thereby to increase its quantity in the keratinocytes in particular, using miRNAs to correct endogenous dysregulations of the miRNAs. The modulation may also be carried out by introducing a modulator for said miRNAs, preferably by introducing at least one miRNA inhibitor, for example an antagomir, targeting one of the miRNAs of the invention in order thereby to reduce its level in the keratinocytes. Other miRNA inhibitors which may in particular be envisaged in the context of this invention are miRCURY LNA™ microRNA Knockdown Probes (Exiqon) and miScript miRNA inhibitors from Qiagen.

In a preferred embodiment, the invention concerns a miRNA selected from the 19 miRNAs of the invention, or a modulator for said miRNA, in particular a miRNA inhibitor, such as an antagomir, targeting said miRNA, for therapeutic use to treat cutaneous pathologies associated with the epidermal differentiation programme. The pathologies concerned are preferably pathologies generating dysfunctions in epidermal differentiation.

More particularly, pathologies that are considered in the context of this invention are psoriasis, atopic dermatitis, acne, ichthyoses, Netherton syndrome, pityriasis rubra pilaris, keratosis pilaris, Darier's disease, palmoplantar keratoderma and porokeratoses.

Preferably, the invention concerns compositions comprising at least two, or even three, preferably at least 5, 10, 15 or equally the 19 miRNAs of the invention, for the therapeutic applications mentioned above, or inhibitors of miRNA, in particular antagomirs of at least some of these miRNAs.

Regarding the therapeutic applications of the invention, if the desired therapeutic effect consists of increasing the state of epidermal differentiation of the skin to be treated, in a preferred embodiment, the invention concerns compositions comprising at least one miRNA selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b, for use in therapy, preferably to treat cutaneous pathologies associated with the epidermal differentiation programme, in particular to treat psoriasis, atopic dermatitis, acne, ichthyoses, Netherton syndrome, pityriasis rubra pilaris, keratosis pilaris, Darier's disease, palmoplantar keratoderma and porokeratoses. The invention also concerns compositions comprising, in addition to or in place of the miRNA or miRNAs cited above, at least one inhibitor of miRNA, such as an antagomir, targeting a miRNA selected from hsa-let-7i, hsa-miR-22, hsa-miR-221, hsa-miR-222, hsa-miR-29a, hsa-miR-29b, hsa-miR-663, hsa-miR-30a and hsa-miR-30c, for use in the treatment of said pathologies. Other inhibitors of miRNA more particularly envisaged in the context of the present invention are miRCURY LNA™ microRNA Knockdown Probes (Exiqon) and miScript miRNA inhibitors from Qiagen.

At least two miRNAs, preferably at least 5, 8 or equally the ten miRNAs from the list consisting of hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b may be selected.

For situations necessitating stimulation of terminal differentiation, a composition or product for the therapeutic application mentioned thus comprises:

at least one, and preferably at least 2, 3, 5 or all of the miRNAs hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b, or modulators of these miRNAs causing an increase in their expression; and/or optionally inhibitors of miRNA, such as antagomirs, targeting one of the miRNAs hsa-let-7i, hsa-miR-22, hsa-miR-221, hsa-miR-222, hsa-miR-29a, hsa-miR-29b, hsa-miR-663, hsa-miR-30a and hsa-miR-30c, or modulators of these miRNAs causing repression of their expression.

More particular inhibitors of miRNA envisaged in the context of this invention are antagomirs, miRCURY LNA™ microRNA Knockdown Probes (Exiqon) and miScript miRNA inhibitors from Qiagen.

In contrast, if the desired therapeutic effect is, for example, to slow down epidermal differentiation, or to promote the proliferative potential of the keratinocytes of the treated skin, in another implementation, the invention concerns compositions comprising at least one miRNA selected from hsa-let-7i, hsa-miR-22, hsa-miR-221, hsa-miR-222, hsa-miR-29a, hsa-miR-29b, hsa-miR-663, hsa-miR-30a and hsa-miR-30c, for therapeutic use, preferably to treat cutaneous pathologies associated with the epidermal differentiation programme, in particular to treat psoriasis, atopic dermatitis, acne, ichthyoses, Netherton syndrome, pityriasis rubra pilaris, keratosis pilaris, Darier's disease, palmoplantar keratoderma and porokeratoses. The invention also concerns compositions comprising, in addition to or in place of the cited miRNA or miRNAs, at least one inhibitor of miRNA, for example an antagomir, targeting a miRNA selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b, for use in the treatment of said pathologies.

At least two miRNAs, preferably at least 4, 7 or equally the nine miRNAs from the list consisting of hsa-let-7i, hsa-miR-22, hsa-miR-221, hsa-miR-222, hsa-miR-29a, hsa-miR-29b, hsa-miR-663, hsa-miR-30a and hsa-miR-30c, may be selected.

In situations necessitating a reduction in terminal differentiation, a composition or product for the mentioned therapeutic application thus comprises:
  at least one, and preferably at least 2, 3, 5 or all of the miRNAs hsa-let-7i, hsa-miR-22, hsa-miR-221, hsa-miR-222, hsa-miR-29a, hsa-miR-29b, hsa-miR-663, hsa-miR-30a and hsa-miR-30c, or modulators of these miRNAs causing an increase in their expression; and/or optionally
  inhibitors of miRNA, for example antagomirs, targeting one of the miRNAs hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b, or modulators of these miRNAs causing repression of their expression.

Inhibitors of miRNA more particularly envisaged in the context of this invention are antagomirs, miRCURY LNA™ microRNA Knockdown Probes (Exiqon) and miScript miRNA inhibitors from Qiagen.

Preferably, the compositions in accordance with the invention for therapeutic use are formulated with pharmaceutically acceptable excipients, for topical application or for ingestion.

The present invention also envisages the use of a miRNA selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425, hsa-miR-92b, hsa-let-7i, hsa-miR-22, hsa-miR-221, hsa-miR-222, hsa-miR-29a, hsa-miR-29b, hsa-miR-663, hsa-miR-30a and hsa-miR-30c, or a modulator of said miRNAs, preferably an inhibitor of miRNA, such as an antagomir, targeting one of said miRNAs, for cosmetic applications to a non-pathological human skin.

The various uses mentioned for therapy or cosmetic use preferably involve local topical application of miRNAs or of a composition comprising said miRNAs, or inhibitors of said miRNAs, for example antagomirs. Because of their small size, the miRNAs and their inhibitors are capable of passing through the membrane of the keratinocytes and of modifying the quantity of said miRNAs in the treated keratinocytes. Further, because of their physico-chemical nature, it is unlikely that they would reach the deep layers of the skin, thus limiting their action to the epidermis.

The stability of miRNAs and their inhibitors, in particular antagomirs, indicates that their action is transitory, and thus the present invention envisages uses in therapy or cosmetics involving renewed applications to the skin to be treated.

For this reason, the invention in particular envisages a method for the treatment of ailments linked to epidermal differentiation in physiological, non-pathological cosmetic situations, comprising the topical application to an individual's skin of a miRNA selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425, hsa-miR-92b, hsa-let-7i, hsa-miR-22, hsa-miR-221, hsa-miR-222, hsa-miR-29a, hsa-miR-29b, hsa-miR-663, hsa-miR-30a and hsa-miR-30c and/or of a modulator of the expression of one of these miRNAs, preferably of an inhibitor of miRNA, for example of an antagomir targeting one of these miRNAs.

In accordance with a preferred embodiment of said method, the miRNA is selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b in order to increase the state of epidermal differentiation of the keratinocytes of the treated skin.

At least two miRNAs may be selected, preferably at least 5, 8 or equally the ten miRNAs from the list consisting of hsa-miR-455-3p, hsa-miR-141, hsa-miR-148a, hsa-miR-182, hsa-miR-224, hsa-miR-26a, hsa-miR-26b, hsa-miR-361-5p, hsa-miR-425, hsa-miR-923 and hsa-miR-92b.

Alternatively or in addition, at least one, or even several inhibitors of miRNA targeting one or more miRNAs selected from hsa-let-7i, hsa-miR-22, hsa-miR-221, hsa-miR-222, hsa-miR-29a, hsa-miR-29b, hsa-miR-663, hsa-miR-30a and hsa-miR-30c, may be chosen. Inhibitors of miRNA more particularly envisaged in the context of this invention are antagomirs, miRCURY LNA™ microRNA Knockdown Probes (Exiqon) and miScript miRNA inhibitors from Qiagen.

In contrast, if the desired effect is, for example, to slow down epidermal differentiation, or to promote the proliferative potential of keratinocytes of the treated skin, in accordance with another embodiment, the invention concerns a treatment method in which said miRNA is selected from hsa-let-7i, hsa-miR-22, hsa-miR-221, hsa-miR-222, hsa-miR-29a, hsa-miR-29b, hsa-miR-663, hsa-miR-30a and hsa-miR-30c.

At least two miRNAs, preferably at least 4, 7 or equally the nine miRNAs from the list consisting of hsa-let-7i, hsa-miR-22, hsa-miR-221, hsa-miR-222, hsa-miR-29a, hsa-miR-29b, hsa-miR-663, hsa-miR-30a and hsa-miR-30c, may be selected.

Alternatively or in addition, at least one, or even several inhibitors of miRNA targeting one or more miRNAs selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425, hsa-miR-923 and hsa-miR-92b, may be chosen. Inhibitors of miRNA more particularly envisaged in the context of this invention are antagomirs, miRCURY LNA™ microRNA Knockdown Probes (Exiqon) and miScript miRNA inhibitors from Qiagen.

Particular epidermal differentiation ailments in cosmetic situations are linked to age, dermatoheliosis, scarring, cutaneous dryness or xerosis, or chemical challenges, in particular from exfoliant agents, desquamating agents, delipidizing agents, or mechanical challenges. These ailments are not pathological and their treatment is not to be considered to be a therapeutic treatment, but only a treatment for cosmetic ends, the treatment of such ailments being essentially aimed at improving the appearance of the skin and the convenience of the individual.

More specifically, the ailments linked to age consist of modifications to epidermal differentiation linked to chronological ageing. In fact, during the ageing process, the epidermis undergoes numerous transformations which affect the epidermal differentiation process and the formation of a functional stratum corneum. Particular observations are thinning of the epidermis, with a more limited number of suprabasal layers and a reduction in the proliferation compartment with a reduction in the number of clonogenic cells, and thus also in epidermal turnover. The markers for conventional differentiation, such as the keratin expression profile, become modified, with expression of keratins 16 and 17 not seen in young, healthy skin. The quantities of keratins K1 and K15 are reduced, as well as that of filaggrin, a principal component of granulous layers. The quantity of transglutaminase 1 also reduces with age. The barrier function is altered, with permeability increasing.

Ailments linked to dermatoheliosis, or 'photo-aging', extend to modifications in epidermal differentiation with chronic exposure to sunlight. A "photo-aged" skin is in particular characterized by an appearance resembling tanned leather and the presence of more pronounced wrinkles; this skin is also modified on an epidermal level, with over-expression of the keratins K6, K16, K17 and a reduction in filaggrin and transglutaminase. These alterations have been associated with the formation of wrinkles. The SPRR proteins involved in the formation of the stratum corneum are also altered by UV. It is also known that acute exposure to the sun results in epidermal modifications affecting the barrier function and epidermal homeostasis.

Ailments linked to scarring extend to modifications in epidermal differentiation with the process of scarring and repair. During the re-epithelialization process occurring after an injury, the entire expression pattern for epidermal proteins is modified. Complete repair occurs in three phases, an initial migration phase, then a proliferation phase and finally a differentiation phase. The proliferation phase covers the wound, and is thus followed by a process of epidermal neo-morphogenesis involving players in keratinocyte stratification and differentiation which, in a healthy situation, can be used to reform a functional stratum corneum.

Ailments linked to dryness or xerosis are principally due to the fact that a dry skin is essentially characterized by a reduction in the lipid content of the epidermis and an alteration in the stratum corneum. Keratins 1 and 10 are reduced and keratinocytes K6 and K14 are increased. The level of expression of filaggrin is perturbed, as is that of involucrin.

Chemical challenges, in particular by exfoliating agents, desquamating agents or delipidizing agents, and mechanical challenges are responsible for modifications to epidermal homeostasis and induce an alteration in the barrier function provided by the stratum corneum. The process of normal epidermal differentiation can re-establish epidermal homeostasis and a normal barrier function.

Upon application, preferably topical, of at least one of the miRNAs of the invention, preferably at least 2, or of a specific inhibitor of said miRNAs, it is possible to treat the various non-pathological ailments mentioned above, for cosmetic applications.

Thus, the present invention is also directed towards cosmetic compositions or products, comprising at least one of the miRNAs of the invention or indeed comprising at least one modulator for the expression of one of the miRNAs of the invention, to correct or improve the appearance of the skin, its grain, its radiance, its imperfections or its micro-relief. A modulator of the expression of one of the miRNAs of the invention is an active ingredient causing an increase or repression in the expression of one of said miRNAs. Said active ingredient modulating the expression of one of the miRNAs is, for example, identified by the screening methods described above, or it is an antagomir of a miRNA of the invention.

The cosmetic product or composition in question may be in any galenical form, for example formulated into a milk, cream, gel, spray or soap, for topical administration, or in a form that can be ingested orally.

In particular, it may be a combination of various active ingredients, for example a combination of at least two miRNAs of the invention, or of a miRNA of the invention and a modulator of a miRNA of the invention, or two miRNA modulators of the invention. It may also be a combination of an active ingredient and an instrument, in particular an instrument of the mechanical, light, or electrical or electromagnetic treatment type.

The present invention in particular envisages cosmetic products known as "anti-ageing" products to reduce surface imperfections linked to disorders in differentiation and the leathery appearance of aged skin. Specific cosmetic products for aged skin exposed to the sun are also envisaged, in order to restore some quality by modifying the balance between proliferation and epidermal differentiation, by means of the miRNAs of the invention or modulators of said miRNAs.

The invention is also directed towards cosmetic after-sun products to counterbalance the modifications in differentiation induces by acute exposure to the sun. Products that can regulate pigmenting disorders by stimulating epidermal differentiation and keratinocyte desquamation are also envisaged in order to more rapidly eliminate the excess melanin responsible for the pigmenting disorder.

Other cosmetic products are also products specifically produced for dry skin, which have a moisturizing effect, and also modulate the terminal steps in epidermal differentiation. Repairing products for improving the cutaneous repair process during scarring are also envisaged in the context of this invention. It is also possible to formulate products for challenged skin, either in the context of specific procedures (post-peeling, post-laser products, etc.) or in day-to-day situations, such as pollution, household products, etc.

In situations necessitating stimulation of terminal differentiation, in order to increase the barrier function and the stratum corneum, a cosmetic composition or product in the sense of the present invention comprises:

at least one, and preferably at least 2, 3, 5 or all of the miRNAs hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b, or modulators of these miRNAs causing an increase in their expression; and/or optionally inhibitors of the miRNAs hsa-let-7i, hsa-miR-22, hsa-miR-221, hsa-miR-222, hsa-miR-29a, hsa-miR-29b, hsa-miR-663, hsa-miR-30a and hsa-miR-30c, or modulators of these miRNAs causing repression of their expression. Inhibitors of miRNA more particularly envisaged in the context of this invention are antagomirs, miRCURY LNA™ microRNA Knockdown Probes (Exiqon) and miScript miRNA inhibitors from Qiagen.

In situations necessitating a reduction in terminal differentiation and a reduction in the formation of the stratum corneum, a cosmetic composition or product in the context of the present invention comprises:

at least one, and preferably at least 2, 3, 5 or all of the miRNAs hsa-let-7i, hsa-miR-22, hsa-miR-221, hsa-miR-222, hsa-miR-29a, hsa-miR-29b, hsa-miR-663, hsa-miR-30a and hsa-miR-30c, or modulators of these miRNAs causing an increase in their expression; and/or optionally inhibitors of the miRNAs hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b, or modulators of these miRNAs causing repression of their expression. Inhibitors of miRNA more particularly envisaged in the context of this invention are antagomirs, miRCURY LNA™ microRNA Knockdown Probes (Exiqon) and miScript miRNA inhibitors from Qiagen.

The present invention also pertains to a kit for determining the state of differentiation of a human keratinocyte, comprising a means for assaying the expression of at least one miRNA selected from hsa-miR-455-3p, hsa-miR-141, hsa-miR-148a, hsa-miR-182, hsa-miR-224, hsa-miR-26a, hsa-miR-26b, hsa-miR-361-5p, hsa-miR-425, hsa-miR-92b, hsa-let-7i, hsa-miR-22, hsa-miR-221, hsa-miR-222, hsa-miR-29a, hsa-miR-29b, hsa-miR-663, hsa-miR-30a and hsa-miR-30c and information providing a reference level for expression of said miRNA or miRNAs.

A particularly preferred kit in the context of the present invention is a kit wherein the reference level is the mean level of expression of said miRNA or miRNAs in non-differentiated keratinocytes under culture.

Alternatively, a kit in accordance with the invention may be used with a reference level which corresponds to the mean level of expression of said miRNA or miRNAs in differentiated epidermal keratinocytes.

The various preferred implementations described more specifically for one or other aspect of the invention are also applicable to other aspects of the invention. In particular, as dictated by the methods, processes, kits, compositions and uses of the invention, it is always preferable to determine the level of expression of at least two miRNAs selected from the list of 19 miRNAs of the invention, preferably at least 3, 5, 9, 10, 15 or even the 19 miRNAs of the invention, namely hsa-miR-455-3p, hsa-miR-141, hsa-miR-148a, hsa-miR-182, hsa-miR-224, hsa-miR-26a, hsa-miR-26b, hsa-miR-361-5p, hsa-miR-425, hsa-miR-92b, hsa-let-7i, hsa-miR-22, hsa-miR-221, hsa-miR-222, hsa-miR-29a, hsa-miR-29b, hsa-miR-663, hsa-miR-30a and hsa-miR-30c.

EXPERIMENTAL SECTION

Materials and Methods

Single Layer Culture of Human Keratinocytes

Normal human epidermal keratinocytes originated from a mammoplasty and were cultivated conventionally using Rheinwald and Green's method, on a nutrient layer of Swiss 3T3 fibroblasts which had been treated with mitomycin.

Reconstructed Skin

Skin reconstructed in vitro comprising a stratified and differentiated epidermis with a stratum corneum and a living equivalent dermis was produced with normal human keratinocytes and normal human dermal fibroblasts.

Briefly, the equivalent dermis was produced with bovine collagen I and one million human dermis fibroblasts. The normal keratinocytes were seeded after contraction of lattices in a quantity of 500000 keratinocytes and cultivated in conventional medium for 7 days. The culture was then mounted on a screen for the emersion phase (air-liquid interface, 7 days).

At the end of this period, the morphology of the skin was very close to normal human skin. It could then be used for the various experiments but keeping the culture medium below the skin, which was nourished by capillary rise.

Extraction of Total RNA from Keratinocytes

Cell Lysis:

The keratinocytes in monolayer culture were lysed in a culture dish in the TriReagent buffer. The reconstructed epidermis from reconstructed skin was separated from the equivalent dermis using tweezers. This epidermis was manually ground in a glass homogenizer in TriReagent lysis buffer.

Extraction of Total RNA

Total RNA was extracted using the conventional technique of lysis in guanidium isothiocyanate solution then extraction using a phenol/chloroform mixture.

miRNA Hybridization on µParaflo™ "MiRHuman 10.0" Chips

The short RNA was extracted from the total RNA (Microcon filter, Millipore) and extended at the 3' end with a polyA tail. A fluorescence-labelled oligonucleotide was ligated to the polyA tail. The short labelled RNA was then hybridized on µParaflo™ "MiRHuman 10.0" chips (Atactic Technologies, LC Sciences). They contained the complementary sequences of all of the human miRNAs recorded in miRBase 10.0 (711 mature miRNAs). The sequences were deposited on the chip 5 times. The fluorescence was quantified and the signals were normalised. The amount of fluorescence reflected the level of expression of each miRNA in the sample.

Statistical Analysis

The expression of each miRNA was compared statistically between the "cultured keratinocytes" sample and the "reconstructed epidermal keratinocyte" sample using the Student t test ($p<0.05$).

EXAMPLE 1

List of 10 miRNA over-expressed in the differentiated reconstructed epidermal keratinocytes compared with the non-differentiated monolayer-cultured keratinocytes.

Three strains of primary normal human keratinocytes from mammoplasty were used in the study (PH202, PH64 and PH63). The expression of all of the known human miRNAs was quantified, in monolayer cultivated keratinocytes, i.e. non-differentiated keratinocytes (2D) and at the same time in the reconstructed epidermal samples with these same keratinocytes (3D).

The expression of each miRNA was compared statistically between the "keratinocytes under culture" sample and the "reconstructed epidermal keratinocyte" sample using the Student t test which provided the probability p. Each miRNA cited in Table 1 had a statistically greater level in the epidermis compared with the non-differentiated keratinocytes ($p<0.05$), for each cell strain being studied. The expression ratio 3D/2D is given for each strain. As an example, miR-141 is on average 2.3 times more abundant in keratinocytes from reconstructed epidermal than in monolayer cultivated keratinocytes.

TABLE 1 miRNAs over-expressed in the keratinocytes of reconstructed epidermis (3D) i.e. differentiated, compared with keratinocytes in monolayer culture (2D), i.e. non-differentiated.

| Name of miRNA | Keratinocytes | 2D Mean signal | 2D Standard deviation | 3D Mean signal | 3D Standard deviation | p_value | Ratio 3D/2D | Mean ratio 3D/2D |
|---|---|---|---|---|---|---|---|---|
| hsa-miR-141 | PH202 | 1047 | 127 | 1930 | 491 | 0.004 | 1.8 | 2.3 |
| | PH64 | 526 | 68 | 1405 | 86 | 0.00002 | 2.7 | |
| | PH63 | 916 | 111 | 2079 | 387 | 0.0002 | 2.3 | |

TABLE 1-continued miRNAs over-expressed in the keratinocytes of reconstructed epidermis (3D) i.e. differentiated, compared with keratinocytes in monolayer culture (2D), i.e. non-differentiated.

| Name of miRNA | Keratinocytes | 2D Mean signal | 2D Standard deviation | 3D Mean signal | 3D Standard deviation | p_value | Ratio 3D/2D | Mean ratio 3D/2D |
|---|---|---|---|---|---|---|---|---|
| hsa-miR-148a | PH202 | 214 | 39 | 619 | 50 | 0.00008 | 2.9 | 4.1 |
| | PH64 | 127 | 37 | 703 | 53 | 0.0002 | 5.5 | |
| | PH63 | 117 | 21 | 466 | 49 | 0.000004 | 4.0 | |
| hsa-miR-182 | PH202 | 538 | 80 | 922 | 94 | 0.0002 | 1.7 | 1.6 |
| | PH64 | 519 | 63 | 873 | 116 | 0.0003 | 1.7 | |
| | PH63 | 530 | 38 | 724 | 58 | 0.0003 | 1.4 | |
| hsa-miR-224 | PH202 | 513 | 108 | 805 | 245 | 0.02 | 1.6 | 1.8 |
| | PH64 | 574 | 164 | 1085 | 278 | 0.005 | 1.9 | |
| | PH63 | 393 | 90 | 723 | 138 | 0.002 | 1.8 | |
| hsa-miR-26a | PH202 | 4673 | 495 | 7757 | 610 | 0.00007 | 1.7 | 1.6 |
| | PH64 | 4370 | 704 | 7025 | 681 | 0.001 | 1.6 | |
| | PH63 | 4616 | 589 | 6707 | 346 | 0.002 | 1.5 | |
| hsa-miR-26b | PH202 | 820 | 106 | 1110 | 82 | 0.004 | 1.4 | 2.0 |
| | PH64 | 654 | 175 | 1390 | 154 | 0.002 | 2.1 | |
| | PH63 | 297 | 67 | 750 | 80 | 0.0005 | 2.5 | |
| hsa-miR-361-5p | PH202 | 337 | 46 | 723 | 37 | 0.0001 | 2.1 | 2.3 |
| | PH64 | 505 | 88 | 1269 | 99 | 0.0001 | 2.5 | |
| | PH63 | 369 | 58 | 853 | 36 | 0.0003 | 2.3 | |
| hsa-miR-425 | PH202 | 339 | 16 | 559 | 41 | 0.00002 | 1.6 | 1.4 |
| | PH64 | 416 | 71 | 551 | 67 | 0.02 | 1.3 | |
| | PH63 | 502 | 44 | 581 | 22 | 0.02 | 1.2 | |
| hsa-miR-455-3p | PH202 | 299 | 38 | 1053 | 96 | 0.0000005 | 3.5 | 3.7 |
| | PH64 | 284 | 64 | 1265 | 187 | 0.00003 | 4.5 | |
| | PH63 | 325 | 50 | 1012 | 83 | 0.00001 | 3.1 | |
| hsa-miR-92b | PH202 | 1104 | 107 | 1632 | 112 | 0.0002 | 1.5 | 1.5 |
| | PH64 | 1487 | 252 | 2400 | 150 | 0.001 | 1.6 | |
| | PH63 | 1482 | 129 | 1906 | 135 | 0.002 | 1.3 | |

EXAMPLE 2

List of the 9 miRNA over-expressed in non-differentiated keratinocytes in monolayer culture compared with differentiated reconstructed epidermal keratinocytes.

3 strains of primary normal human keratinocytes from a mammoplasty were used in the study (PH202, PH64 and PH63). The expression of all of the known human miRNAs was quantified in the keratinocytes cultivated as a monolayer, i.e. non-differentiated keratinocytes and at the same time in the reconstructed epidermis with these same keratinocytes.

The expression of each miRNA was compared statistically between the "cultured keratinocytes" sample and the "reconstructed epidermal keratinocyte" sample using the Student t test which produced the probability p. Each miRNA cited in this table had a statistically greater level in the non-differentiated keratinocytes compared with the reconstructed epidermal keratinocytes (p<0.05), for each cell strain studied. The expression ratio 2D/3D is given for each strain. As an example, miR-29b was on average 6.7 times more abundant in monolayer cultivated keratinocytes than in the reconstructed epidermal keratinocytes.

TABLE 2 miRNAs over-expressed in keratinocytes in monolayer culture (2D), i.e. non-differentiated, compared with the keratinocytes of reconstructed epidermis (3D) i.e. differentiated.

| Name of miRNA | Keratinocytes | 2D Mean signal | 2D Standard deviation | 3D Mean signal | 3D Standard deviation | p_value | Ratio 2D/3D | Mean ratio 2D/3D |
|---|---|---|---|---|---|---|---|---|
| hsa-let-7i | PH202 | 2947 | 77 | 1211 | 111 | 0.00003 | 2.4 | 2.4 |
| | PH64 | 2573 | 297 | 1208 | 157 | 0.00002 | 2.1 | |
| | PH63 | 3125 | 179 | 1178 | 90 | 0.0000001 | 2.7 | |
| hsa-miR-22 | PH202 | 2668 | 241 | 2316 | 96 | 0.03 | 1.2 | 1.4 |
| | PH64 | 2497 | 436 | 1645 | 155 | 0.004 | 1.5 | |
| | PH63 | 3661 | 361 | 2386 | 155 | 0.0002 | 1.5 | |
| hsa-miR-221 | PH202 | 5556 | 792 | 3184 | 175 | 0.0005 | 1.7 | 2.0 |
| | PH64 | 3213 | 774 | 1844 | 117 | 0.01 | 1.7 | |
| | PH63 | 5558 | 360 | 2321 | 75 | 0.000001 | 2.4 | |
| hsa-miR-222 | PH202 | 6069 | 637 | 3022 | 195 | 0.00002 | 2.0 | 2.4 |
| | PH64 | 3901 | 303 | 1867 | 106 | 0.000001 | 2.1 | |
| | PH63 | 7763 | 505 | 2580 | 170 | 0.00000003 | 3.0 | |
| hsa-miR-29a | PH202 | 7593 | 1191 | 3826 | 357 | 0.00023 | 2.0 | 3.0 |
| | PH64 | 9569 | 1407 | 2624 | 550 | 0.00001 | 3.6 | |
| | PH63 | 11055 | 291 | 3258 | 272 | 0.00001 | 3.4 | |

TABLE 2-continued miRNAs over-expressed in keratinocytes in monolayer culture (2D), i.e. non-differentiated, compared with the keratinocytes of reconstructed epidermis (3D) i.e. differentiated.

| Name of miRNA | Keratinocytes | 2D Mean signal | 2D Standard deviation | 3D Mean signal | 3D Standard deviation | p_value | Ratio 2D/3D | Mean ratio 2D/3D |
|---|---|---|---|---|---|---|---|---|
| hsa-miR-29b | PH202 | 1070 | 116 | 192 | 13 | 0.0000001 | 5.6 | 6.7 |
|  | PH64 | 734 | 136 | 96 | 40 | 0.0002 | 7.7 |  |
|  | PH63 | 947 | 60 | 135 | 18 | 0.0000007 | 7.0 |  |
| hsa-miR-663 | PH202 | 1537 | 157 | 564 | 31 | 0.000002 | 2.7 | 2.0 |
|  | PH64 | 1090 | 199 | 691 | 129 | 0.008 | 1.6 |  |
|  | PH63 | 2053 | 241 | 1233 | 110 | 0.0001 | 1.7 |  |
| hsa-miR-30a | PH202 | 707 | 46 | 404 | 28 | 0.000004 | 1.7 | 1.9 |
|  | PH64 | 787 | 104 | 504 | 147 | 0.02 | 1.6 |  |
|  | PH63 | 901 | 89 | 374 | 38 | 0.000003 | 2.4 |  |
| hsa-miR-30c | PH202 | 1667 | 111 | 990 | 77 | 0.00001 | 1.7 | 1.6 |
|  | PH64 | 2260 | 325 | 1315 | 115 | 0.0004 | 1.7 |  |
|  | PH63 | 1619 | 216 | 1215 | 109 | 0.009 | 1.3 |  |

EXAMPLE 3

Methods for Detecting miRNAs

Northern Blot:

This conventional technique is qualitative and quantitative. It can analyze several miRNAs during one experiment. This method requires the use of 5 to 50 μg of total RNA.

RT Q-PCR

This method can study precursors of miRNAs and has been adapted to study mature miRNAs. It is a commercial method (Applied Biosystems TaqMan MicroRNA Assays) and has been described in several articles [23].

miRNA Microarray

This method, like that of microarrays for conventional mRNA, is based on the fluorescent labelling of the complementary cDNA of the miRNAs of a sample, and hybridization of these labelled cDNA on a slide onto which known miRNA sequences have been deposited [25].

According to some authors, if it regularly integrates novel sequences of miRNAs derived from miRBase, this miRNA microarray technique should be the method of choice for the analysis of the overall expression profile of miRNAs.

In addition, in some situations as in the present invention, the expression profile of the miRNAs is more informative than the expression profile of messenger RNA.

In Situ Hybridization of miRNAs

This technique is more difficult than the conventional in situ hybridization of mRNA since using the conventional binding method, short RNAs diffuse more than long RNAs and are lost during the hybridization and washing steps. Techniques have been developed to overcome this problem; in addition, miRNA probes are commercially available (Exiqon, Denmark) [27].

miRNA Reporter Transgene

In this technique, a GFP or LacZ reporter gene was placed under the control of a promoter including the complementary 3'UTR portion of a miRNA.

BIBLIOGRAPHY

1. Bartel D P. MicroRNAs: genomics, biogenesis, mechanism, and function. *Cell* 2004; 116: 281-97.
3. Alvarez-Garcia I, Miska E A. MicroRNA functions in animal development and human disease. *Development* 2005; 132: 4653-62.
4. O'Donnell K A, Wentzel E A, Zeller K I et al. c-Myc-regulated microRNAs modulate E2F1 expression. *Nature* 2005; 435: 839-43.
5. Fazi F, Rosa A, Fatica A et al. A minicircuitry comprised of microRNA-223 and transcription factors NFI-A and C/EBPalpha regulates human granulopoiesis. *Cell* 2005; 123: 819-31.
8. Yi R, O'Carroll D, Pasolli H A et al. Morphogenesis in skin is governed by discrete sets of differentially expressed microRNAs. *Nat Genet.* 2006; 38: 356-62.
10. Wenguang Z, Jianghong W, Jinquan L et al. A subset of skin-expressed microRNAs with possible roles in goat and sheep hair growth based on expression profiling of mammalian microRNAs. *OMICS.* 2007; 11: 385-96.
11. Yi R, Poy M N, Stoffel M et al. A skin microRNA promotes differentiation by repressing 'stemness'. *Nature* 2008; 452: 225-9.
12. Sonkoly E, Wei T, Janson P C et al. MicroRNAs: Novel Regulators Involved in the Pathogenesis of Psoriasis? *PLoS. ONE.* 2007; 2: e610.
13. Felicetti F, Errico M C, Bottero L et al. The promyelocytic leukemia zinc finger-microRNA-221/-222 pathway controls melanoma progression through multiple oncogenic mechanisms. *Cancer Res* 2008; 68: 2745-54.
14. Ishida-Yamamoto A, Tanaka H, Nakane H et al. Inherited disorders of epidermal keratinization. *J Dermatol Sci* 1998; 18: 139-54.
15. Hoffjan S, Stemmler S. On the role of the epidermal differentiation complex in ichthyosis vulgaris, atopic dermatitis and psoriasis. *Br J Dermatol* 2007; 157: 441-9.
17. Ghadially R, Brown B E, Sequeira-Martin S M et al. The aged epidermal permeability barrier. Structural, functional, and lipid biochemical abnormalities in humans and a senescent murine model. *J. Clin. Invest* 1995; 95: 2281-90.
18. Harding C R. The stratum corneum: structure and function in health and disease. *Dermatol Ther* 2004; 17 Suppl 1: 6-15.
19. Marionnet C, Bernerd F, Dumas A et al. Modulation of gene expression induced in human epidermis by environmental stress in vivo. *J Invest Dermatol* 2003; 121: 1447-58.
23. Chen C, Ridzon D A et al. Real-time quantification of microRNAs by stem-loop RT-PCR. *Nucleic Acids Res* 2005; 33: e179.

25. Vagin V V et al. A distinct small RNA pathway silences selfish genetic elements in the germline. *Science* 2006; 313: 320-324.

27. Takada S et al. Mouse microRNA profiles determined with a new and sensitive cloning method. *Nucleic Acids Res* 2006; 34: e115.

The invention claimed is:

1. A method for determining the state of epidermal differentiation of a human keratinocyte in a sample of human epithelium, the method comprising:
   producing a reconstructed skin with normal human keratinocytes and normal human dermal fibroblasts;
   determining a level of expression of at least one miRNA selected from the group consisting of hsa-miR-455-3p, hsa-miR-141, hsa-miR-148a, hsa-miR-182, hsa-miR-224, hsa-miR-26a, hsa-miR-26b, hsa-miR-361-5p, hsa-miR-425, hsa-miR-92b, hsa-let-7i, hsa-miR-22, hsa-miR-221, hsa-miR-222, hsa-miR-29a, hsa-miR-29b, hsa-miR-663, hsa-miR-30a and hsa-miR-30c, within a human keratinocyte of the reconstructed skin;
   comparing the level of expression of the selected miRNA or miRNAs with a mean level of expression of the selected miRNA or miRNAs in non-differentiated keratinocytes under culture, or in differentiated epidermal keratinocytes; and
   concluding that the keratinocyte is differentiated if a level of expression of at least one miRNA selected from the group consisting of hsa-miR-455-3p, hsa-miR-141, hsa-miR-148a, hsa-miR-182, hsa-miR-224, hsa-miR-26a, hsa-miR-26b, hsa-miR-361-5p, hsa-miR-425 and hsa-miR-92b is statistically greater than a mean level of expression of said miRNA in non-differentiated keratinocytes under culture, or
   concluding that the keratinocyte is non-differentiated if a level of expression of at least one miRNA selected from the group consisting of hsa-let-7i, hsa-miR-22, hsa-miR-221, hsa-miR-222, hsa-miR-29a, hsa-miR-29b, hsa-miR-663, hsa-miR-30a and hsa-miR-30c is statistically greater than a mean level of expression of said miRNA in differentiated epidermal keratinocytes.

2. A method for screening modulators of the epidermal differentiation process in an epithelium, the method comprising evaluating a state of epidermal differentiation of keratinocytes in said epithelium with the method of claim 1, before and after application of a modulator to be screened.

3. The method of claim 2, wherein said modulator is a chemical originating from a natural extract, a complex formulation, a DNA molecule, a miRNA, a siRNA, a miRNA inhibitor, an antagomir or an instrumental system employing radiation.

4. The method of claim 3, wherein the modulator is identified if it causes a modification of the level of expression of at least two of said miRNAs in the epithelium.

5. A kit for determining the state of differentiation of a human keratinocyte in a reconstituted skin culture epithelium, the kit comprising an assay for determining the expression of at least one miRNA selected from the group consisting of hsa-miR-455-3p, hsa-miR-141, hsa-miR-148a, hsa-miR-182, hsa-miR-224, hsa-miR-26a, hsa-miR-26b, hsa-miR-361-5p, hsa-miR-425, hsa-miR-92b, hsa-let-7i, hsa-miR-22, hsa-miR-221, hsa-miR-222, hsa-miR-29a, hsa-miR-29b, hsa-miR-663, hsa-miR-30a and hsa-miR-30c and information providing a reference level for expression of said miRNA or miRNAs.

6. The method of claim 1, wherein the comparing occurs against a mean level of expression of the selected miRNA or miRNAs in non-differentiated keratinocytes under culture, or in differentiated epidermal keratinocytes, which non-differentiated keratinocytes or differentiated epidermal keratinocytes having originated from the same strain or the same population.

7. The method of claim 2, wherein said modulator is a chemical originating from an instrumental system employing visible, UV, IR or X radiation.

* * * * *

```
                            SEQUENCE LISTING

<160> NUMBER OF SEQ ID NOS: 19

<210> SEQ ID NO 1
<211> LENGTH: 22
<212> TYPE: RNA
<213> ORGANISM: homo sapiens

<400> SEQUENCE: 1
uaacacuguc ugguaaagau gg                                              22

<210> SEQ ID NO 2
<211> LENGTH: 22
<212> TYPE: RNA
<213> ORGANISM: homo sapiens

<400> SEQUENCE: 2
ucagugcacu acagaacuuu gu                                              22

<210> SEQ ID NO 3
<211> LENGTH: 24
<212> TYPE: RNA
<213> ORGANISM: homo sapiens

<400> SEQUENCE: 3
uuuggcaaug guagaacuca cacu                                            24

<210> SEQ ID NO 4
<211> LENGTH: 21
<212> TYPE: RNA
<213> ORGANISM: homo sapiens

<400> SEQUENCE: 4
caagucacua gugguuccgu u                                               21

<210> SEQ ID NO 5
<211> LENGTH: 22
<212> TYPE: RNA
<213> ORGANISM: homo sapiens

<400> SEQUENCE: 5
uucaaguaau ccaggauagg cu                                              22

<210> SEQ ID NO 6
<211> LENGTH: 21
<212> TYPE: RNA
<213> ORGANISM: homo sapiens

<400> SEQUENCE: 6
uucaaguaau ucaggauagg u                                               21

<210> SEQ ID NO 7
<211> LENGTH: 22
<212> TYPE: RNA
<213> ORGANISM: homo sapiens

<400> SEQUENCE: 7
uuaucagaau cuccaggggu ac                                              22

<210> SEQ ID NO 8
```

```
<211> LENGTH: 23
<212> TYPE: RNA
<213> ORGANISM: homo sapiens

<400> SEQUENCE: 8
aaugacacga ucacucccgu uga                                              23

<210> SEQ ID NO 9
<211> LENGTH: 21
<212> TYPE: RNA
<213> ORGANISM: homo sapiens

<400> SEQUENCE: 9
gcaguccaug ggcauauaca c                                                21

<210> SEQ ID NO 10
<211> LENGTH: 22
<212> TYPE: RNA
<213> ORGANISM: homo sapiens

<400> SEQUENCE: 10
uauugcacuc gucccggccu cc                                               22

<210> SEQ ID NO 11
<211> LENGTH: 22
<212> TYPE: RNA
<213> ORGANISM: homo sapiens

<400> SEQUENCE: 11
ugagguagua guuugugcug uu                                               22

<210> SEQ ID NO 12
<211> LENGTH: 22
<212> TYPE: RNA
<213> ORGANISM: homo sapiens

<400> SEQUENCE: 12
aagcugccag uugaagaacu gu                                               22

<210> SEQ ID NO 13
<211> LENGTH: 23
<212> TYPE: RNA
<213> ORGANISM: homo sapiens

<400> SEQUENCE: 13
agcuacauug ucugcugggu uuc                                              23

<210> SEQ ID NO 14
<211> LENGTH: 21
<212> TYPE: RNA
<213> ORGANISM: homo sapiens

<400> SEQUENCE: 14
agcuacaucu ggcuacuggg u                                                21

<210> SEQ ID NO 15
<211> LENGTH: 22
<212> TYPE: RNA
<213> ORGANISM: homo sapiens

<400> SEQUENCE: 15
uagcaccauc ugaaaucggu ua                                               22
```

```
<210> SEQ ID NO 16
<211> LENGTH: 23
<212> TYPE: RNA
<213> ORGANISM: homo sapiens

<400> SEQUENCE: 16
uagcaccauu ugaaaucagu guu                                              23

<210> SEQ ID NO 17
<211> LENGTH: 22
<212> TYPE: RNA
<213> ORGANISM: homo sapiens

<400> SEQUENCE: 17
aggcggggcg ccgcgggacc gc                                               22

<210> SEQ ID NO 18
<211> LENGTH: 22
<212> TYPE: RNA
<213> ORGANISM: homo sapiens

<400> SEQUENCE: 18
uguaaacauc cucgacugga ag                                               22

<210> SEQ ID NO 19
<211> LENGTH: 23
<212> TYPE: RNA
<213> ORGANISM: homo sapiens

<400> SEQUENCE: 19
uguaaacauc cuacacucuc agc                                              23
```